United States Patent [19]  [11]  4,356,267
Callegaro et al.  [45]  Oct. 26, 1982

[54] ENZYME IMMOBILIZATION IN CELLULOSIC HOLLOW FIBRES

[75] Inventors: Lanfranco Callegaro, Padova; Antonio Boniolo, Saluggia; Ennio Denti, Pino Torinese; Umberto Rosa, Turin; Valdano Rossi, San Benedetto Po, all of Italy

[73] Assignee: Sorin Biomedica S.p.A., Saluggia, Italy

[21] Appl. No.: 233,702

[22] Filed: Feb. 12, 1981

[30] Foreign Application Priority Data

Feb. 13, 1980 [IT] Italy ............................ 67212 A/80
Feb. 12, 1981 [IT] Italy ............................ 67023 A/81

[51] Int. Cl.$^3$ .................. C12N 11/12; C12M 1/40; B01D 13/00
[52] U.S. Cl. .................. 435/179; 210/321.3; 210/927; 435/269; 435/288
[58] Field of Search ............ 435/174, 177, 178, 179, 435/182, 288, 269; 210/655, 321.3, 927

[56] References Cited

U.S. PATENT DOCUMENTS 3,228,877  1/1966  Mahon .................. 210/321.3 X
3,706,633  12/1972  Katchalski et al. .............. 435/178
3,715,277  2/1973  Dinelli et al. .................. 435/182
3,947,352  3/1976  Cuatrecasas et al. ............ 435/178 X
4,013,514  3/1977  Wildi et al. .................. 435/179 X
4,261,828  4/1981  Brunner et al. ................ 435/288 X
4,266,026  5/1981  Breslan ...................... 435/288 X

FOREIGN PATENT DOCUMENTS 1224947  3/1971  United Kingdom .
2020668  11/1979  United Kingdom .

OTHER PUBLICATIONS

Sundaram et al., Preparation and Properties of Urease Chemically Attached to Nylon, FEBS Letters, vol. 10, No. 5, 1970, (pp. 325–327).

*Primary Examiner*—David M. Naff
*Attorney, Agent, or Firm*—Sughrue, Mion, Zinn, Macpeak & Seas

[57] ABSTRACT

Enzymes are immobilized in a bundle of cellulosic hollow fibres for use as a fibre-bundle dialyzer for purifying blood. Immobilization is carried out by circulating through the lumen of the fibres to activate the fibres an aqueous solution of sodium periodate at a concentration of 0.7–21 mg/ml, a circulation rate of 300–500 mm$^3$/minute/mm$^2$, a temperature of 15°–30° C. and for a period not exceeding 70 minutes, removing excess sodium periodate by washing the fibres, and directly or indirectly anchoring an enzyme to the activated fibres. Washing is preferably carried out by circulating through the lumen of the fibres dionized water followed by a dilute aqueous solution of glycerol. The fibres containing an immobilized enzyme may be sterilized with a sterilizing agent.

20 Claims, No Drawings

ENZYME IMMOBILIZATION IN CELLULOSIC HOLLOW FIBRES

This invention applies to purification of blood by circulating the latter in an extracorporeal circuit including a dialyzer comprising a bundle of cellulosic hollow fibres.

As is known, dialyzers of this type have proven to be very practical and efficient. The fibre bundle typically comprises some thousands (e.g. 8,000) of hollow (tubular) fibres wherein the lumen of each fibre has a diameter of the order of 200-300 microns and wherein the wall of each fibre is of a very small thickness, of the order of 10-20 microns and constitutes the semipermeable membrane for the dialysis process. In operation, the blood circulates through the lumen of the fibres, from one end to the other of the bundle, while the acqueous dialysis liquid is circulated through the interspaces between the fibre. The length of the fibres typically amounts to about 25-30 cm and is selected (together with the number of fibres) so as to provide an adequate effective area for dialysis, generally of from 0.6 to 1.3 $m^2$.

It is also known that the substances to be removed from the blood may comprise (and frequently comprise) toxic substances of which the passage through the membrane(s) of a dialyzer is difficult or even impossible, either because of their excessive molecular weight or because of their lipophilic, rather than hydrophilic, character. This class of substances comprises, for example, various pesticides, epoxydic compounds and phenolic compounds or derivates. A healthy human organism contains enzymes capable of converting such substances into dialysable products by reactions such as oxidation, hydrolysis or conjugation. When such enzymes are absent, or when their activity is insufficient to combat an intoxication, purification of blood by extracorporeal dialysis becomes practically impossible. A tentative remedy consists in immobilizing the necessary enzyme (previously isolated e.g. from an animal liver) on a solid support thereby to obtain a material usable in a "reactor" inserted into the extracorporeal circuit in series with the dialyzer.

The problem of immobilization of enzymes on solid supports was intensively investigated in the art. The following references appear to be relevant:

ENZYME ENGINEERING, Vol. 3, pages 43-49 and 397-408 (Plenum Press, New York and London), METHODS OF ENZYMOLOGY, Vol. XLIV "Immobilized Enzymes" (Academic Press) pages 551-555 and 930-934, APPLIED BIOCHEMISTRY AND BIOENGINEERING, Vol. 1, "Immobilized Enzyme Principles", pages 69-73 (Academic press), British Pat. No. 1,224,947 (Snam Progetti),
British Pat. No. 2,020,668 (Snam Progetti),
U.S. Pat. No. 3,519,538 (R. A. Messing et al.).

Thus, various modes of immobilization were developed depending i.a. upon the nature of the support and upon the degree of risk that an enzyme may become disactivated (denatured) during immobilization process. The support may be of a particulate form, as was suggested for the material commercially known as "Sepharose", of cellulosic nature, or in the form of synthetic fibres. The art also discloses "reactors" comprising a bundle of tubes or hollow fibres, and further discloses studies on immobilization of enzymes within the wall of a tube or fibre or solely on the inside (lumen surface) thereof. In the latter case the art proposes nylon tubes with impervious wall, having inner diameter of 0.8 mm and wall thickness of 0.2 mm. Moreover, according to the references cited hereinbefore, the enzyme may be chemically bound to the support either directly or indirectly through a purposely interposed chemical grouping (the so-called "spacer arm") typically consisting of a bifunctional amine moiety to which the amino-group of the enzyme is bonded with the use of an aldehyde (in practice, glutaraldehyde). It is also known that an enzyme may be anchored to the support through a covalent bond. For example, in connection with "Sepharose", it was proposed to activate the hydroxyl groups of this support by means of an activating agent such as cyanogen bromide or by means of an oxidizing agent such as sodium periodate ($NaIO_4$), removing excess agent by washing and reacting the enzyme with the hydroxyl groups activated in this manner.

For the details of the expedients just indicated above attention of the reader is directed to the references listed hereinbefore, the relevant content of which should be regarded as making part of this specification.

The primary object of this invention is to immobilize a convenient enzyme on the lumen surface of hollow cellulosic fibres forming a bundle in or for a blood dialyzer of fibre bundle type whereby, when haematic flow is circulated through the dialyzer, a non-dialyzable undesired substance contained in the flow may be converted by the enzyme into a dialyzable product removable through the semipermeable walls of the fibres.

The prior art teachings result insufficient in this respect. More particularly, it was not possible to date to obtain on the lumen surfaces of the dialyzer bundle a sufficient amount active enzyme without fatal prejudice to both the physico-chemical (particularly mechanical), dialyzing and bio-compatibility characteristics of the fibres. In a hollow fibre employed in the "reactor" mentioned hereinbefore the wall of the fibre has no dialyzing function and its thickness may be increased at will to values sufficient to avoid failure in practical use. Also the material of the fibre may be conveniently selected among these most suitable for a "reactor". All this, however, is not true in the specific case of a hollow fibre bundle dialyzer, in which the material and structure of the fibre walls shall absolutely comply with the requisites of haemodialysis, and wherein the membranes formed by the walls of the fibres are "ultra-thin" due to their thickness generally not exceeding 0.05 mm, preferably not exceeding 0.02 mm.

This invention is based upon a discovery that its object stated hereinbefore may be attained through covalent anchorage to the lumen surfaces provided that, basically, activation of the cellulose support or substrate is effected under specific conditions.

Accordingly, this invention provides a method of immobilizing an enzyme in a bundle of cellulosic hollow fibres in or for a fibre-bundle dialyzer for purifying blood, by a process comprising a stage (a) of activating a cellulosic material by means of an oxidizing agent, a subsequent stage (b) of removing excess agent by washing, and a still subsequent stage (c) of directly or indirectly anchoring the enzyme to the activated material through covalent linkages, characterized in that, for the purpose of anchoring the enzyme selectively to the lumen surfaces of the fibres, the activating state (a) is effected by circulating through the lumen of the fibres in the bundle an aqueous solution of sodium periodate at a concentration of 0.7–21 mg/ml, at a circulation rate of 300–500 mm$^3$/minute referred to 1 mm$^2$ of cross-sectional area of the lumen, at a temperature of 15°–30° C. for a period of time not exceeding 70 minutes.

Preferably, the concentration of sodium periodate does not exceed 5 mg/ml, and a recommendable concentration is about 1 mg/ml. Also preferably, the circulation rate is from 350 to 480 mm$^3$/min/mm$^2$, and a recommendable rate is about 400 mm$^3$/min/mm$^2$. The activation is preferably effected at room temperature that is, at 18°–25° C. If convenient, higher temperatures may be adopted; however, at temperatures exceeding 30° C. the oxidizing action of the periodate involves an increasing risk of deterioration of the fibres. The activation time is in inverse relationship both with the temperature and with the concentration of the periodate. Attention should be paid to not substantially exceed (accidentally) 70 minutes, because with an activation time of 80 minutes the fibres generally become unusable.

By operating under the conditions indicated above high enzyme concentrations on the lumen surfaces are obtained, while the cellulosic walls underlaying said surfaces remain practically intact and preserve their original characteristics of strength, bio-compatibility and dialyzing efficiency.

In practice, as is known, a bundle of hollow cellulosic fibres for a haemodialyzer has a form of a "cartridge", in which the fibres extend between and through a pair of headplates, similarly to the bundle of tubes in a heat exchanger. The headplates typically consist of a cast in situ polyurethane resin forming a thick terminal desk through which the individual fibres open to the outside. In use, the headplates are sealingly clamped in the body of the dialyzer thereby to separate the haematic circuit (including the lumens of the fibres) from the dialysis liquid circuit (including the interspaces between the fibres in the cartridge). The blood being dialyzed reaches the cartridge at the outer face of one of the headplates, then passes through the cartridge by flowing through the lumens of the component fibres, and outflows from the other headplate. Therefore, the method according to this invention may be worked in practice by circulating the treating liquids through the lumens of the fibres while the cartridge is in loco in the body of the dialyzer, and the same expedient also applies to the stages (b) and (c). Alternatively, instead of the dialyzer body, a purposely designed equivalent container may be employed.

Prior to the activation the fibres preferably should be conditioned by means of deionized water, to saturate the fibres with water and purge them. This can be done by flowing deionized water through the lumens of the fibres at a circulation rate of e.g. 500–1000 mm$^3$/min/mm$^2$ for about ten minutes. Concerning the objects of the method according to this invention, conditioning is advantageous and important to avoid that the activating solution be undesirably absorbed into the walls of the fibres with consequent undesirable oxidation in depth of the walls.

According to the invention, also the stage (b) of washing after activation should preferably be effected under specific conditions. More particularly, washing should produce at first a quick stoppage of the oxidation process and subsequently an accurate removal of last traces of the periodate. Therefore, according to the invention, the washing step is effected by circulating through the lumen of the fibres at first deionized water for a total volume amounting to at least 10 times (preferably 20 times) the total volume of the lumens of the fibres, and subsequently a dilute aqueous solution of glycerol, preferably at a concentration of from 8 vol.% to 15 vol.%. The prior art suggests washing with ethylene glycol; the latter, however, can hardly be regarded as non-toxic and, moreover, is not an effective "quenching" agent for the oxidation reaction. A recommendable concentration of glycerol is 10 vol.%, which not only eliminates from the fibres last traces of the periodate but also appears to be the best suited for bringing the cellulosic material of the fibres to physico-chemical equilibrium conditions.

The invention is applicable to all enzymes in human bio-engineering field, capable of converting non-dialyzable substances into dialyzable products. In particular, enzymes of the ligandin series, such as glutathione transferase, and enzymes such as creatininase, asparaginase, uricase, beta-galactoxydase and arginase may be mentioned.

As was stated hereinbefore, the covalent anchorage to the activated support may be direct, or indirect through a bifunctional amine.

For direct anchorage it is advisable, according to the invention, to preliminarily treat the fibres with a buffer solution in the basic range of pH values, from 7.0 to 9.0, preferably from 8.0 to 8.5, still preferably 8.4. This treatment increases the yield of immobilization of the enzyme. To this end, an aqueous solution of sodium bicarbonate 0.1 M (pH 8.4) may be circulated through the lumens of the fibres for about 10 minutes. After this pre-treatment, an aqueous solution of the desired enzyme is circulated through the lumens at a low temperature, generally not exceeding 8° C., for several hours until no further absorption of the enzyme is noted. The concentration of the enzymic solution is not critical, but values of from 0.5 to 2.0 mg/ml are preferred. The circulation time amounts, as average, to about 12 hours. The circulation rate may be selected within wide limits, but is preferably equal to that used in the activation stage. The Schiff base formed in this manner between the aldehydic groups resulting from activation of the cellulosic support and the amino-groups of the enzyme is then reduced (to form the desired covalent bond) by treatment with a reducing aqueous solution, particularly with a solution of sodium boro-hydride. To this end, it is convenient to add the boro-hydride to the circulating enzymic solution and to continue circulation for at least one further hour, still at the low temperature indicated hereinbefore. The concentration of the boro-hydride may be from 0.5 to 2 mg/ml, but preferably is about 1 mg/ml. This treatment rapidly stabilizes the enzyme/support bond without any prejudice for the support and/or release of harmful or dangerous by-products. At the end of the treatment, excess solution in the fibres can be removed by circulating through the lumens an aqueous solution of a high ionic power providing a buffer typical for the involved enzyme; e.g., for a ligandin a buffer at pH 7.4 may be employed consisting of potassium phosphate 10 mM and EDTA (ethylenediamino tetracetic acid) 1 mM and containing potassium chloride 0.1 M.

For indirect anchorage, the pre-treatment with a basic buffer is not absolutely necessary. In particular, the reaction with the bifunctional amine can be carried out even at a pH below 7.0 generally not below 5.), provided that the pH value selected for the reaction exceeds the last acidic pH value of the employed amine.

Suitable bifunctional amines are 3,3'-diaminodipropylamine and tri-, tetra-, penta- and hexamethylenediamines, for example. The amine is employed in aqueous solution, generally at a concentration from 0.5 M to 1.3 M, preferably 1 M, and circulation is effected at room temperature (18°–20° C.) for several hours, typically 18 hours, at a moderate circulation rate, for example 200–400 mm$^3$/min/mm$^2$. Subsequently, the fibre bundle is cooled to a low temperature, e.g. 4° C., the amine solution is brought to a pH from 8 to 9, for example by addition of solid sodium carbonate, whereupon the reducing agent (preferably sodium borohydride) is added to obtain a concentration value indicated hereinbefore, and circulation of the obtained solution through the lumens of the fibres is continued for 1–5 hours, typically about 3 hours. The circulation rate may be of from about 200 to about 600 mm$^3$/min/mm$^2$, but preferably amounts to 400 mm$^3$/min/mm$^2$. Thereafter, the fibres are returned to room temperature and washed by flowing (both internally and externally) at first deionized water, then an aqueous solution of a salt of a high ionic power, preferably potassium chloride 1 M, and finally again deionized water. For example, with the bundle of 8000 fibres described hereinbefore, washing may be effected at first with 5 liters deionized water at a circulation rate of 200 ml/min, then with 5 liters KCl solution at a rate of 100 ml/min, and finally again with 5 liters deionized water at a rate of 100 ml/min. After the washing stage, the lumens of the fibres are treated by circulating therethrough an aqueous solution of glutaraldehyde at a concentration of from 1% to 12% by volume, buffered at pH 8.0 with potassium phosphate 50 mM. The circulation is effected at room temperature, typically for about one hour, at a rate of 300–500 mm$^3$/min/mm$^2$, ordinarily 400 mm$^3$/min/mm$^2$. Subsequently the fibres are washed, both internally and externally, by circulation of a volume of water corresponding to 10–20 times the total volume of the lumens at a circulation rate of 200 ml/minute, whereupon the fibres are equilibrated by circulation of a coupling buffer, preferably sodium carbonate 0.1 M, pH 8.3. At this point, the enzymic solution is circulated through the lumens at low temperature (e.g. 4° C.), at a concentration of 0.5–2 mg/ml for 10–12 hours. The circulation rate is as for the direct anchorage. Then the lumens of the fibres are washed by circulation of an aqueous saline solution of high ionic power not harmful to the enzyme (such as, for arginase, Tris-HCl 10 mM, pH 7.5, containing MnCl$_2$ 5 mM and KCl 1 M) at a rate of 400–800 mm$^3$/min/mm$^2$, and by a subsequent circulation of an amino-acidic buffer solution, for example glycine 0.1 M, at a rate of 200–400 mm$^3$/min/mm$^2$. Finally, preferably, the fibres are equilibrated by flowing through the lumens a buffer having a stabilizing effect on the employed enzyme; for example, in case of arginase, a suitable buffer is Tris-HCl 10 mM, pH 7.5, containing MnCl$_2$ 5 mM.

The conditions described above for both directly and indirectly anchoring the enzyme are those producing an absolutely irreversible immobilization of the enzyme. However, it is to be understood that indications provided by the art and indications contained herein may suggest those skilled in the art to introduce eventually various modifications and adaptations convenient for every specific case.

Various aspects of details of the method according to the invention will result from the following examples.

In all examples use was made of a dialyzer SPIRAFLO (Sorin Biomedica S.p.A.) with an exchangeable cartridge comprising 800 hollow fibres of CUPROPHAN (R.T.M.) of Enka Glanzstoff A.G., having inner diameter of 200 microns, wall thickness of 11 microns and a length of 26 cm. With these data, the cross-sectional area of the lumen of each fibre was 0.0314 mm$^2$, with resulting total cross-sectional area of 251 mm$^2$ and total volume of 65.26 ml, of the lumens. Therefore, to a total liquid flow of 100 ml/minute through the lumens of the fibres corresponded a circulation rate of 400 mm$^3$/minute per 1 mm$^2$ of lumen area, and to each fraction or multiple of said flow corresponded an identical fraction or multiple of said rate. The total dialyzing area was 1.3 m$^2$. In every case, prior to activation, the fibres were conditioned at room temperature by circulating through the lumens deionized water at a total flow of 200 ml/minute for a total volume of 2 liters.

EXAMPLE 1

Direct anchorage of Glutathione-S-Transferase

Aqueous solution of sodium periodate at a concentration of 1 mg/ml is circulated through the lumens of the fibres at a rate of 100 ml/min for one hour at room temperature (18°–20° C.). Thereafter, the bundle is emptied and the lumens are washed at first by circulation of deionized water at a rate of 200 ml/min for a total volume of 1.5 liters, then by circulation of aqueous glycerol (concentration 10 vol.%) at a rate of 100 ml/min for a total volume of 5 liters, whereupon the fibres are pretreated by circulating therethrough a buffer solution of sodium bicarbonate 0.1 M (pH 8.4).

At the end of the pre-treatment there is circulated through the lumens, for 12 hours at 4° C., an aqueous solution of glutathione-S-transferase, obtained from porc liver, at a concentration of 1.3 mg/ml. Thereafter, the circulating solution is additioned with sodium borohydrite to a concentration of about 1 mg/ml and circulation is continued for a further one hour. At this point final washing is effected with a buffer solution pH 7.4 constituted by potassium phosphate 10 mM, potassium chloride 0.1 M and EDTA 1 mM.

The amount enzyme immobilized in this manner in the lumens of the bundle of fibres is capable of metabolizing in one hour, at a flow rate of 170 ml/min, 115 mg of 1-chloro-2,4-dinitrobenzene under standard test conditions reported by the literature (J. Biol. Chem. 249, 7.130, 1974).

Evaluation of the effective irreversibility of the bond between the cellulosic support and an enzyme, obtained in the above manner, was done with the use of two methods:

1.—immobilization in CUPROPHAN fibres of human albumin labeled with I[125] and ascertainment of any released radioactivity, and 2.—immobilization in CUPROPHAN fibres of human immunoglobulins and subsequent dosage of any release of these proteins with the use of an immunoenzymatic tracer (anti-human immunoglobulin peroxydase).

In both cases, a circulation through the dialyzer lumens of human serum at 37° C. for 4 hours did not yield results indicating a release of the immobilized protein.

Cartridges having immobilized therein the glutathione-S-transferase in accordance with this Example were tested as to both the clearance (in vitro) and ultrafiltration, and the results are tabulated in Tables 1 and 2 hereinbelow. The tabulated values show, i.a., that the procedure described in this Example did not substantially affect the ultrafiltration characteristics of the fibres. The tabulated values represent each an average of 10 test runs. The tests concerning Table 2 were effected at 37° C., at a venous pressure nil (zero) and with a flow dialyzing solution of 500 ml/minute. The Tables 1 and 2 also report results obtained with periodate concentrations of 5 mg/ml and 21 mg/ml in the activating solution. The values reported in columns 3,4,5 and 6 of the Table 2 are are conventionally expressed in ml/hour.

EXAMPLE 3

Indirect anchorage of Arginase

Activation with sodium periodate (5 mg/ml) and washing with water and aqueous glycerol are effected in the manner described in Example 1.

The dialyzer is then evacuated and subjected to circulation through the fibre lumens of an aqueous solution of 3,3'-diamino-dipropylamine at a flow rate of 50 ml/minute for 18 hours at room temperature. Thereafter, the temperature of the dialyzer is lowered to 4° C., the pH value of the amine solution is brought to 9.0 by

TABLE 1

| | CLEARANCE (ml/min) OF THE DIALYZER OF EXAMPLE 1. | | | | | | | | | | | | | | | | | | | |
|---|---|---|---|---|---|---|---|---|---|---|---|---|---|---|---|---|---|---|---|---|
| | URIC ACID (M.W. 165) | | | | CREATININE (M.W. 113) | | | | UREA (M.W. 60) | | | | VITAM.$B_{12}$ (M.W. 1355) | | | | PHOSPHATES (M.W. 95) | | | |
| | HAEMATIC FLOW ml/min | | | | | | | | | | | | | | | | | | | |
| CARTRIDGE | 75 | 150 | 200 | 300 | 75 | 150 | 200 | 300 | 75 | 150 | 200 | 300 | 75 | 150 | 200 | 300 | 75 | 150 | 200 | 300 |
| BLANKS (AVERAGE) | 65 | 90 | 104 | 111 | 69 | 101 | 118 | 133 | 75 | 136 | 155 | 182 | | 29 | | 31 | 60 | 83 | 90 | 100 |
| $NaIO_4$ (1 mg/ml) | 68 | 105 | 124 | 139 | 70 | 118 | 140 | 156 | 76 | 134 | 160 | 194 | | 29 | | 31 | 62 | 93 | 104 | 112 |
| $NaIO_4$ (5 mg/ml) | 55 | 74 | 84 | 90 | 61 | 85 | 99 | 105 | 70 | 112 | 127 | 161 | | 25 | | 27 | 51 | 67 | 73 | 80 |
| $NaIO_4$ (21 mg/ml) | 45 | 65 | 71 | 78 | 51 | 74 | 86 | 95 | 70 | 119 | 133 | 148 | | 17 | | 19 | 43 | 56 | 61 | 69 |

TABLE 2

ULTRAFILTRATION OF THE DIALYZER OF EXAMPLE 1

| 1 | 2 | 3 | 4 | 5 | 6 |
|---|---|---|---|---|---|
| | | CARTRIDGE | | | |
| Neg. Press. (mmHg) | Haematic Flow (ml/min) | Blanks (average) | $NaIO_4$ (1 mg/ml) | $NaIO_4$ (5 mg/ml) | $NaIO_4$ (21mg/ml) |
| 0 | 75 | 97 | 96 | 98 | 95 |
| | 150 | 135 | 135 | 137 | 130 |
| | 100 | 164 | 163 | 168 | 161 |
| | 300 | 219 | 220 | 225 | 215 |
| 50 | 75 | 245 | 240 | 260 | 230 |
| | 150 | 293 | 282 | 310 | 279 |
| | 200 | 317 | 313 | 340 | 308 |
| | 300 | 373 | 371 | 400 | 363 |
| 100 | 75 | 474 | 460 | 505 | 445 |
| | 150 | 517 | 504 | 542 | 493 |
| | 200 | 545 | 530 | 575 | 525 |
| | 300 | 598 | 591 | 639 | 585 |
| 200 | 75 | 971 | 960 | 990 | 870 |
| | 150 | 1010 | 1008 | 1038 | 911 |
| | 200 | 1041 | 1031 | 1060 | 947 |
| | 300 | 1100 | 1090 | 1118 | 1014 |
| 100 | 75 | 1454 | 1457 | 1475 | 1343 |
| | 150 | 1500 | 1525 | 1525 | 1385 |
| | 200 | 1529 | 1545 | 1551 | 1420 |
| | 300 | 1590 | 1600 | 1621 | 1481 |

EXAMPLE 2

Direct anchorage of Creatininase

The procedure is as in Example 1, with the use of a solution of creatininase (creatinine-aminohydrolase from Alcaligenes species). The amount of enzyme immobilized in this manner is capable of metabolizing at room temperature 18 micromols/minute of creatinine. The physico-chemical, dialyzing and bio-compatibility properties of the hollow fibres in the dialyzer do not result appreciably changed.

addition of solid powdered sodium carbonate and the solution is additioned with sodium boro-hydrate to a concentration of 1 mg/ml. This solution is circulated through the lumens of the fibres for further 3 hours, at the indicated temperature and at a flow rate of 100 ml/minute. The fibres are then returned to room temperature and washed internally and externally at first with 5 liters water at a rate of 200 ml/minute, then with 5 liters aqueous potassium chloride 1 M at a rate of 100 ml/minute, and finally again with 5 liters water at a rate of 100 ml/minute. Subsequently, a circulation is made through the lumens of the fibres, for one hour at room temperature, of a solution of glutaraldehyde (concentration 3 vol.%) in a buffer potassium phosphate 50 mM, pH 8.0, at a rate of 100 ml/minute. After this treatment the fibres are washed internally and externally with 1.5 liters water at a rate of 200 ml/minute, and equilibrated by circulating through the lumens a coupling buffer (sodium bicarbonate 0.1 M, pH 8.3) at a rate of 150 ml/minute for 10 minutes.

At this point, the dialyzer is brought to 4° C. and a circulation is effected through the fibre lumens for 12 hours of an arginase solution at a concentration of 1 mg/ml. Finally, the lumens are washed at room temperature at first by circulation of Tris-HCl 10 mM, pH 7.5, containing $MnCl_2$ 5 mM and KCl 1 M, at a rate of 200 ml/minute, and subsequently by circulation of aqueous glycine 0.1 M for 0.5 hours at a rate of 100 ml/minute, whereupon the fibres are equilibrated by circulating therethrough Tris-HCl 10 mM containing $MnCl_2$ 5 mM, pH 7.5, for 0.5 hours at a rate of 100 ml/minute.

With this treatment, the physico-chemical, dialyzing and bio-compatibility properties of the fibres result practically, unchanged. The amount arginase immobilized in this manner is capable of metabolizing 230 micromols/minute arginine under standard test conditions (Anal. Biochem. 22, 518, 1968). Irreversibility of the support/enzyme bond was ascertained by the methods indicated in Example 1. The values of clearance and ultrafiltration are reported in Tables 5 and 6, respectively. Moreover, Tables 7 and 8 report corresponding values obtained with the use in the activating stage of a sodium periodate solution at a concentration of 21 mg/ml.

TABLE 5

| | CLEARANCE (ml/min) OF THE DIALYZER OF EXAMPLE 3. | | | | | | | | | | | | | | | | | | |
|---|---|---|---|---|---|---|---|---|---|---|---|---|---|---|---|---|---|---|---|
| | URIC ACID | | | | CREATININE | | | | UREA | | | | VITAM. B$_{12}$ | | | | PHOSPHATES | | |
| | Haematic flow (ml/min) | | | | | | | | | | | | | | | | | | |
| CARTRIDGE | 75 | 150 | 200 | 300 | 75 | 150 | 200 | 300 | 75 | 150 | 200 | 300 | 75 | 150 | 200 | 300 | 75 | 150 | 200 | 300 |
| Blanks (average) | 65 | 90 | 103 | 111 | 68 | 89 | 114 | 126 | 76 | 135 | 154 | 181 | — | 29 | | 31 | 59 | 80 | 86 | 98 |
| With Enzyme | 52 | 70 | 81 | 91 | 57 | 73 | — | 96 | 72 | 112 | 122 | 143 | — | 19 | — | 21 | 51 | 70 | 76 | 84 |

TABLE 6

ULTRAFILTRATION OF THE DIALYZER OF EXAMPLE 3

| 1 | 2 | 3 | 4 |
|---|---|---|---|
| Neg. Press. (mmHg) | Haematic flow (ml/min) | CARTRIDGE | |
| | | Blanks (average) | With enzyme |
| 0 | 75 | 98 | 85 |
| | 150 | 136 | 117 |
| | 200 | 166 | 139 |
| | 300 | 220 | 189 |
| 50 | 75 | 249 | 190 |
| | 150 | 292 | 229 |
| | 200 | 318 | 260 |
| | 300 | 371 | 312 |
| 100 | 75 | 489 | 411 |
| | 150 | 534 | 448 |
| | 200 | 552 | 475 |
| | 300 | 618 | 530 |
| 200 | 75 | 982 | 795 |
| | 150 | 1025 | 839 |
| | 200 | 1052 | 861 |
| | 300 | 1110 | 914 |
| 300 | 75 | 1488 | 1240 |
| | 150 | 1431 | 1277 |
| | 200 | 1559 | 1300 |
| | 300 | 1618 | 1353 |

TABLE 7

| | CLEARANCE (ml/min) OF THE DIALYZER OF EXAMPLE 3 ACTIVATED WITH 21 mg/ml NaIO$_4$ | | | | | | | | | | | | | | | | | | | |
|---|---|---|---|---|---|---|---|---|---|---|---|---|---|---|---|---|---|---|---|---|
| | URIC ACID | | | | CREATININE | | | | UREA | | | | VITAM.B$_{12}$ | | | | PHOSPHATES | | | |
| | Haematic flow | | | | | | | | | | | | | | | | | | | |
| CARTRIDGE | 75 | 150 | 200 | 300 | 75 | 150 | 200 | 300 | 75 | 150 | 200 | 300 | 75 | 150 | 200 | 300 | 75 | 150 | 200 | 300 |
| BLANKS (average) | 65 | 90 | 103 | 111 | 68 | 99 | 114 | 126 | 76 | 135 | 154 | 181 | — | 29 | — | 31 | 59 | 80 | 86 | 98 |
| With enzyme | 50 | 72 | 79 | 90 | 52 | 74 | 84 | 94 | 63 | 97 | 109 | 128 | — | 15 | — | 16 | 52 | 69 | 72 | 81 |

TABLE 8

ULTRAFILTRATION OF THE DIALYZER OF EXAMPLE 3 ACTIVATED WITH 21 mg/ml NaIO$_4$

| 1 | 2 | 3 | 4 |
|---|---|---|---|
| Neg. Press. (mmHg) | Haematic Flow (ml/min) | CARTRIDGE | |
| | | Blanks (average) | With enzyme |
| 0 | 75 | 98 | 80 |
| | 150 | 136 | 115 |
| | 200 | 166 | 140 |
| | 300 | 220 | 195 |
| 50 | 75 | 249 | 220 |
| | 150 | 292 | 240 |
| | 200 | 318 | 270 |
| | 300 | 371 | 321 |
| 100 | 75 | 489 | 390 |
| | 150 | 534 | 442 |
| | 200 | 558 | 463 |
| | 300 | 618 | 520 |
| 200 | 75 | 982 | 800 |
| | 150 | 1025 | 830 |
| | 200 | 1052 | 860 |

TABLE 8-continued

ULTRAFILTRATION OF THE DIALYZER OF EXAMPLE 3 ACTIVATED WITH 21 mg/ml NaIO$_4$

| 1 | 2 | 3 | 4 |
|---|---|---|---|
| Neg. Press. (mmHg) | Haematic Flow (ml/min) | CARTRIDGE | |
| | | Blanks (average) | With enzyme |
| | 300 | 1110 | 915 |
| 300 | 75 | 1488 | 1200 |
| | 150 | 1531 | 1235 |
| | 200 | 1559 | 1265 |
| | 300 | 1618 | 1320 |

EXAMPLE 4

Indirect anchorage of Asparaginase

The procedure is as in Example 3, with the use of an aqueous solution of asparaginase at a concentration of 1 mg/ml. The amount of enzyme immobilized in this manner in the dialyzer is capable of metabolizing 290 micromols/minute asparagine in standard test conditions described in the literature (Biochem. Biophys. Res. Comm. 12, 50, 1963). As in the preceding Examples, the fibre bundle processed in this manner and duly sterilized is perfectly usable in extracorporeal dialysis without any release of the enzyme.

EXAMPLE 5

Indirect anchorage of beta-Galactoxydase

The procedure is as in Example 3, with the use of an aqueous solution of beta-galactoxydase at a concentration of 1 mg/ml. The amount of enzyme immobilized in this manner in the dialyzer is capable of metabolizing 30 micromols/minute of o-nitrophenyl-beta-D-galactopyranoside under standard test conditions described in the literature (J. Biol. Chem. 240, 2468, 1965).

EXAMPLE 6

Indirect anchorage of uricase

The procedure is as in Example 3, with the use of an aqueous solution of uricase at a concentration of 1 mg/ml. The amount of enzyme immobilized in this manner is capable of metabolizing 0.44 micromols/minute uric acid under standard test conditions described in the literature (Comp. Biochem. Physiol. B. Comp. Biochem. 57, 33, 1977).

EXAMPLE 7

Indirect anchorage of Deoxyribonuclease

The procedure is as in Example 3, with the use of an aqueous solution of deoxyribonuclease at a concentration of 1 mg/ml. The amount of enzyme immobilized in this manner is capable of metabolizing 32 mg/hour of DNA.

EXAMPLE 8

Indirect anchorage of Catalase

The procedure is as in Example 3, with the use of catalase in lieu of arginase, and with the use of hexamethylenediamine in lieu of 3,3'-diamino-dipropylamine. The amount of enzyme immobilized in this manner is 73 mg and is capable of producing 2.2 mg/minute of molecular oxygen from 100 ml of $H_2O_2$ 0.014 M.

EXAMPLE 9

(Comparative)

The procedure of Example 1 is repeated with the use, as activating agent, of cyanogen bromide at concentrations varying from 0.7 to 21 mg/ml. The fibre bundles processed in this manner resulted unusable in extracorporal dialysis due to impossibility of anchoring the enzyme in irreversible manner.

EXAMPLE 10

(Comparative)

The procedure of Example 1 was repeated with the use of sodium periodate solutions at concentrations beyond the limits indicated hereinbefore, that is, (i) of 0.5 mg/ml and (ii) of 25 mg/ml. As a result, in case (i) metabolization of 1-chloro-2,4-dinitro benzene decreased to insignificant values, whereas in case (ii) the mechanical and dialzying properties of the fibres were reduced to practically unacceptable values.

EXAMPLE 11

(Comparative)

The procedure of Example 1 was repeated with circulation rates of the periodate solution of 200 and 600 $mm^3/min/mm^2$, respectively. In both cases, each repeated 5 times, disruptions of fibres under dialysis conditions occured.

In practical use of the present invention the bundle of fibres having the enzyme immobilized therein shall be sterilized prior to its use in extracorporeal dialysis, and it is known that sterilization processes applied to date in the field of immobilized enzyme inevitably imply a drastic degradation (even to 100%) of the enzyme. Moreover, in the present case, the sterilization conditions may unacceptably affect the properties of the fibres. Still moreover, there is a problem of anyhow avoiding the event that the sterilization conditions may lead to formation of toxic by-products, particularly those not removable by dialysis.

According to the invention, in order to avoid unacceptable loss of activity of the immobilized enzyme, the sterilization is effected by exposing the bundle of fibres to an external sterilizing agent while the fibres are filled with a buffer solution which is specific to the involved enzyme on account of its stabilizing effect, said solution optionally containing glycerol as protective agent for the fibres. Preferably, the sterilization is effected by exposing the bundle to gamma-radiations at a dose of 2.5 Mrad ± 10% or to a gaseous mixture of ethylene oxide with a "Freon", preferably "Freon 12" (dichloro-difluoro-methane).

EXAMPLE 12

The fibres of the bundle obtained in accordance with Example 1 are filled with a buffer typical for glutathione-S-transferase, formed by potassium phosphate 10 mM, pH 7.0, reduced glutathione 5 mM, EDTA 1 mM, with a 30 vol.% glycerol content, the latter ingredient being purposely added as protective agent for the fibres. Sterilization is effected by exposing the bundle to gamm-radiation 2.5 Mrad for 72 hours. With this treatment, the chemico-physical, dialyzing and bio-compatibility properties of the fibres remain practically unchanged. The activity of the enzyme results reduced solely by 55%.

EXAMPLE 13

The fibres of the bundle obtained in Example 4 are filled with a buffer typical for asparaginase, formed by potassium phosphate 50 mM, pH 7.4, and reduced glutathione 5 mM. The sterilization is effected by external contact of the fibres with a gaseous sterilizing mixture formed by 12 vol.% of ethylene oxide and 88 vol.% of "Freon 12", with a relative humidity value of 50%. This operation is effected for 4 hours at 45° C. in a chamber in which the pressure of the gaseous mixture amounts to 0.6 atmospheres gauge. Thereafter, the bundle is degased in a degassing chamber (in accordance with conventional health rules) for 24 hours at 40° C. and for further 10 days at room temperature. The physico-chemical, dialysing and bio-compatibility properties of the fibres result practically unchanged. The activity of the enzyme is reduced solely by 30%.

We claim:

1. A method for immobilizing an enzyme in a bundle of cellulosic hollow fibres for a fibre-bundle dialyzer for purifying blood, comprising the following sequential steps:
   (a) activating said cellulosic hollow fibres by circulating through the lumen of the fibres in the bundle an aqueous solution of sodium periodate at a concentration of 0.7–2.1 mg/ml, at a circulation rate of 300–500 $mm^3/minute/mm^2$ at a temperature of 15°–30° C. for a period of time not exceeding 70 minutes.
   (b) removing excess sodium periodate by circulating through the lumens of the fibres in the bundle deionized water to a total volume amounting to at least 10 times the total volume of the lumens of the fibres, and subsequently circulating a dilute aqueous solution of glycerol to the lumens of the fibres in the bundle; and
   (c) directly or indirectly anchoring the enzyme to the activated cellulosic fibres through covalent linkages.

2. Method according to claim 1, wherein the periodate concentration does not exceed 5 mg/ml.

3. Method according to claim 1, wherein the periodate concentration is 1 mg/ml.

4. Method according to claim 1, wherein the circulation rate is 350–480 $mm^3/min/mm^2$.

5. Method according to claim 4, wherein the circulation rate is 400 $mm^3/min/mm^2$.

6. Method according to claim 1, wherein the temperature is from 18° C. to 25° C. and the time period is of 60 minutes.

7. Method according to claim 1, wherein the lumen diameter of the fibres is from 200 to 300 microns and the wall thickness of the fibres is 10–20 microns.

8. Method according to claim 1, wherein the enzyme is a glutathione transferase.

9. Method according to claim 1, wherein the enzyme is creatininase.

10. Method according to claim 1, wherein the enzyme is asparaginase.

11. Method according to claim 1, wherein the enzyme is beta-galactoxydase.

12. Method according to claim 1, wherein the enzyme is uricase.

13. Method according to claim 1, wherein the enzyme is arginase.

14. Method according to claim 1, wherein the glycerol concentration in the said solution is from 8 to 15 vol.%.

15. Method according to claim 1, wherein the glycerol concentration in said solution is 10 vol.%.

16. Method according to claim 1, wherein the fibre bundle containing the immobilized enzyme is sterilized by exposing the fibres to an external sterilizing agent while the fibres are filled with a buffer solution specific to the enzyme.

17. Method according to claim 16, wherein the sterilization is effected by exposing the fibres to a gamma-radiation at a dosage of 2.5 Mrad.

18. Method according to claim 16, wherein the sterilization is effected by exposing the fibres to a gaseous mixture of ethylene oxide and a "Freon".

19. Method according to claim 18, wherein the gaseous mixture consists of 12 vol.% of ethylene oxide and 88 vol.% of "Freon" 12.

20. Method according to claims 16 or 17, wherein the buffer solution additionally comprises glycerol as protective agent for the fibres.

* * * * *